US00PP22227P2

(12) United States Plant Patent
O'Connell

(10) Patent No.: US PP22,227 P2
(45) Date of Patent: Nov. 1, 2011

(54) ***ALOE* PLANT NAMED 'PICKLED PINK'**

(50) Latin Name: ***Aloe* hybrid**
Varietal Denomination: Pickled Pink

(76) Inventor: Renee O'Connell, Escondido, CA (US)

( * ) Notice: Subject to any disclaimer, the term of this patent is extended or adjusted under 35 U.S.C. 154(b) by 124 days.

(21) Appl. No.: 12/455,717

(22) Filed: Jun. 6, 2009

(51) Int. Cl.
*A01H 5/00* (2006.01)

(52) U.S. Cl. ..... Plt./443
(58) Field of Classification Search ..... Plt./443
See application file for complete search history.

*Primary Examiner* — Annette H Para

(57) ABSTRACT

A new and distinct *Aloe* cultivar named 'Pickled Pink' is disclosed, characterized a very papillose texture to leaves, jewel-like appearance to leaves with bright coral leaf margins and papillae; overlaid with glaucous blue green patina. Plants are very floriferous and exhibit an upright morphology. The new variety is an *Aloe,* typically produced as a garden or container plant.

1 Drawing Sheet

Latin name of the genus and species: *Aloe* hybrid.
Variety denomination: 'Pickled Pink'.

BACKGROUND OF THE INVENTION

The new cultivar is a product of a planned breeding program. The new variety originated from a cross pollination of the seed parent, an unpatented proprietary selection of *Aloe*× *rauhii*×*parvula* referred to as 'P' with the pollen parent an unpatented proprietary selection of, *Aloe parvula*×*capitata* referred to as '*Parvula* hybrid #5'. The crossing was made during March of 2006 in Vista, Calif., at a commercial greenhouse. 'Pickled Pink' was discovered by the inventor, Renee O'Connell, in November of 2006, in Vista, Calif. at a commercial greenhouse.

Asexual reproduction of the new cultivar 'Pickled Pink' was first performed in Vista, Calif., at a commercial greenhouse by vegetative leaf cuttings in February 2007. 'Pickled Pink' has since produced several generations and has shown that the unique features of this cultivar are stable and reproduced true to type.

SUMMARY OF THE INVENTION

The cultivar 'Pickled Pink' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Pickled Pink.' These characteristics in combination distinguish 'Pickled Pink' as a new and distinct *Aloe* cultivar:

1. Very papillose texture to leaves.
2. Jewel-like appearance to leaves with bright coral leaf margins and papillae; overlaid with glaucous blue green patina.
3. Very floriferous.
4. Upright morphology.
5. Unusual coral margins and papillae almost appear fluorescent at certain angles.

PARENTAL COMPARISON

Plants of the new cultivar 'Pickled Pink' are similar to the seed parent 'P' in most horticultural characteristics. However, 'Pickled Pink' exhibits a coral pink margin and papillae, not observed in 'P.' Additionally, 'Pickled Pink' exhibits more leaf papillae than 'P' and 'Pickled Pink' exhibits a blue-green patina, combined with a bright coral margin and textured papillae, not observed 'P'. 'Pickled Pink' is also more floriferous than *Aloe* hybrid 'P'.

Plants of the new cultivar 'Pickled Pink' are similar to the pollen parent '*Parvula* hybrid #5' in most horticultural characteristics. However 'Pickled Pink' exhibits a coral pink margin and papillae, not exhibited in '*Parvula* hybrid #5.' Additionally, 'Pickled Pink' is more floriferous than *Parvula* hybrid #5, and has a more compact and upright morphology.

COMMERCIAL COMPARISON

'Pickled Pink' can be compared to the unpatented commercial variety *Aloe* 'Black Beauty.' Plants of *Aloe* 'Black Beauty' are similar to plants of 'Pickled Pink' in most horticultural characteristics, however, 'Pickled Pink' produces more offsets, and a more upright plant. Additionally, 'Pickled Pink' has intense pink margins and papillae not observed in 'Black Beauty.''Pickled Pink' is also more floriferous than 'Black Beauty'.

'Pickled Pink' can also be compared to the unpatented commercial variety *Aloe* 'Midnight.' Plants of *Aloe* 'Midnight' are similar to plants of 'Pickled Pink' in most horticultural characteristics, however, 'Pickled Pink' produces a significantly more upright plant and has foliage that produces a brighter pink margin. Additionally, 'Pickled Pink' produces more offsets and is more floriferous than 'Black Beauty'.

BRIEF DESCRIPTION OF THE PHOTOGRAPH

The accompanying photograph in FIG. 1 illustrates in full color a typical plant of 'Pickled Pink' grown outdoors in Vista, Calif. This plant is approximately 7 months old, shown in a 4 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to the Pantone Process Color System Guide, except where general terms of ordinary dictionary significance are used. The following observations and measurements describe 'Pickled Pink' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 3000 fc of light. Measurements and numerical values represent averages of typical plant types.
Botanical classification: *Aloe* hybrid 'Pickled Pink'.
Age of the plant described: Approximately 9 months.

PROPAGATION

Time to initiate roots: About 20 days at approximately 21° C.
Root description: Fibrous.
Propagation method: Vegetative divisions.

PLANT

Growth habit: Succulent, rosulate plant.
Container size: 4 inch.
Height: Approximately 9 cm to top of highest leaf.
Plant spread: Approximately 14 cm.
Growth rate: Slow.
Branching characteristics: Offsets.

FOLIAGE

Leaf:
*Arrangement.*—Alternate, rosulate.
*Average length.*—Approximately 8 cm.
*Widest width.*—Approximately 2 cm.
*Width at base.*—1 cm.

FOLIAGE

Leaf:
*Shape of blade.*—Lanceolate.
*Apex.*—Acute.
*Base.*—Rounded.
*Margin.*—Undulate, somewhat serrate, with unevenly dispersed cartilaginous serrulate teeth.
*Texture of top surface.*—Rugose, papillate.
*Texture of bottom surface.*—Papillate.
*Quantity of leaves per plant.*—Approximately 21.
*Color.*—Young foliage upper side, background color: Near S 321-2 Pantone. Young foliage, upper side, papillae: Near S 107-2 Pantone. Young foliage under side, background: Near S 202-7 321-2 check. Yong foliage, underside, papillae: Near S 107-2 Pantone. Young foliage, margin: Near S 107-2 Pantone. Mature foliage upper side, background color: Near S 321-1 Pantone. Mature foliage, under side, glaucous color: Near S 202-7 Pantone. Mature foliage under side, background color: Near S 321-2. Mature foliage, where glaucous color is removed: Near S 308-5 Pantone. Mature foliage, margin color: Near S 107-2 Pantone.
*Venation.*—Type: Linear. Venation color upper side: Near S 15-7 Pantone. Venation color under side: Near S 15-8 Pantone.

FLOWER

Natural flowering season: Various times of year; more frequently during late winter-spring.
Inflorescence type and habit: Heterothetic raceme.
Rate of flower opening: One every several days.
Flower longevity on plant: 2-3 days.
Quantity of flowers: Average 23 fully opened flowers at one time.
Total inflorescence size:
*Height.*—Approximately 37.95 cm.
*Width.*—Approximately 0.343 cm.
Corolla:
*Arrangement.*—Arranged in 2 whorls of 3 petals each.
*Size.*—Length: Approximately 2.08 cm. Width: Approximately 0.76 cm at widest point. Lobe Length: Approximately 2.01 cm. Lobe Width: Approximately 0.479 cm.
*Margin.*—Entire.
*Shape.*—Oblong.
*Apex.*—Acute.
*Texture.*—Smooth.
Color: Tepals: when opening: Outer surface: Base color near S 90-2 Pantone. Mid tepal color near S 90-3 Pantone. Tip color near S 9-07 Pantone. Midrib line color near S 308-1 Pantone. Inner surface: Base color near S 90-3 Pantone. Mid tepal color near S 90-4 Pantone. Tip color near S 90-6 Pantone. Midrib stripe color near S 308-2 Pantone. Fully opened: Outer surface: Base color near S 90-3 Pantone. Mid tepal color near S 90-4 Pantone. Tip color near S 90.8 Pantone. Midrib stripe color near S 308-1. Inner surface: Base color near S 90-4 Pantone. Mid tepal color near S 90-4 Pantone. Tip color near S 90-8 Pantone. Midrib stripe color near S 308-2 Pantone. Color Changes when Aging: Near S 91.3 base to mid tepal color.
Sepals: Not present.
Bud:
*Shape.*—Oblong.
*Length.*—Between 1.98 cm. at lowest bud to 0.5 cm at apical bud. Diameter: Between 0.56 cm at lowest bud to 0.18 cm at apical bud. Color: Base color near S 90-2 Pantone. Mid tepal color near S 90-3 Pantone. Tip color near S 9-07 Pantone. Midrib line color near S 308-1 Pantone.
Pedicels: Length: Approximately 1.1 to 1.34 cm. Width: Approximately 0.087 to 0.094 cm. Aspect: Slanted. Color: Between S 93-3 and S 92-3 Pantone.
Scape: Length: Approximately 38 cm. Width: Approximately 0.335 xm. Angle: Acute with respect to leaves. Strength: Moderately flexible, but strong. Color: Near S 321-8 Pantone. Fragrance: None.

REPRODUCTIVE ORGANS

Stamens:
*Number.*—Average 6.
*Filament length.*—Between 1.62 and 0.1.7 cm.
*Filament color.*—Near S 91-7 Pantone.
*Anther length.*—Between 0.305 and 0.255 cm.
*Anther color.*—Near S 53-1 Pantone.
*Anther shape.*—Oblong.
*Pollen.*—Near S 50-1 Pantone.
Pistil:
*Number.*—1.
*Length.*—Approximately 1.25 to 1.6 cm.
*Style color.*—Near S 57-4 Pantone.

*Stigma.*—Shape: Elliptical. Color: Near S 313-3 Pantone. Ovary color: Near S 313-4 Pantone.

OTHER CHARACTERISTICS

Seeds and fruits: Fruit is oblong, approximately 0.8 cm diameter, with 3 carpals.

Disease/pest resistance: Neither resistance nor susceptibility to normal diseases and pests of *Aloe* has been observed.

Temperature tolerance: Tolerates temperatures from approximately −1 C to 32 C.

Drought tolerance: Tolerates at least 2 weeks of high temperatures without supplemental water, showing no serious damage to plant.

What is claimed is:

1. A new and distinct cultivar of *Aloe* plant named 'Pickled Pink' as herein illustrated and described.

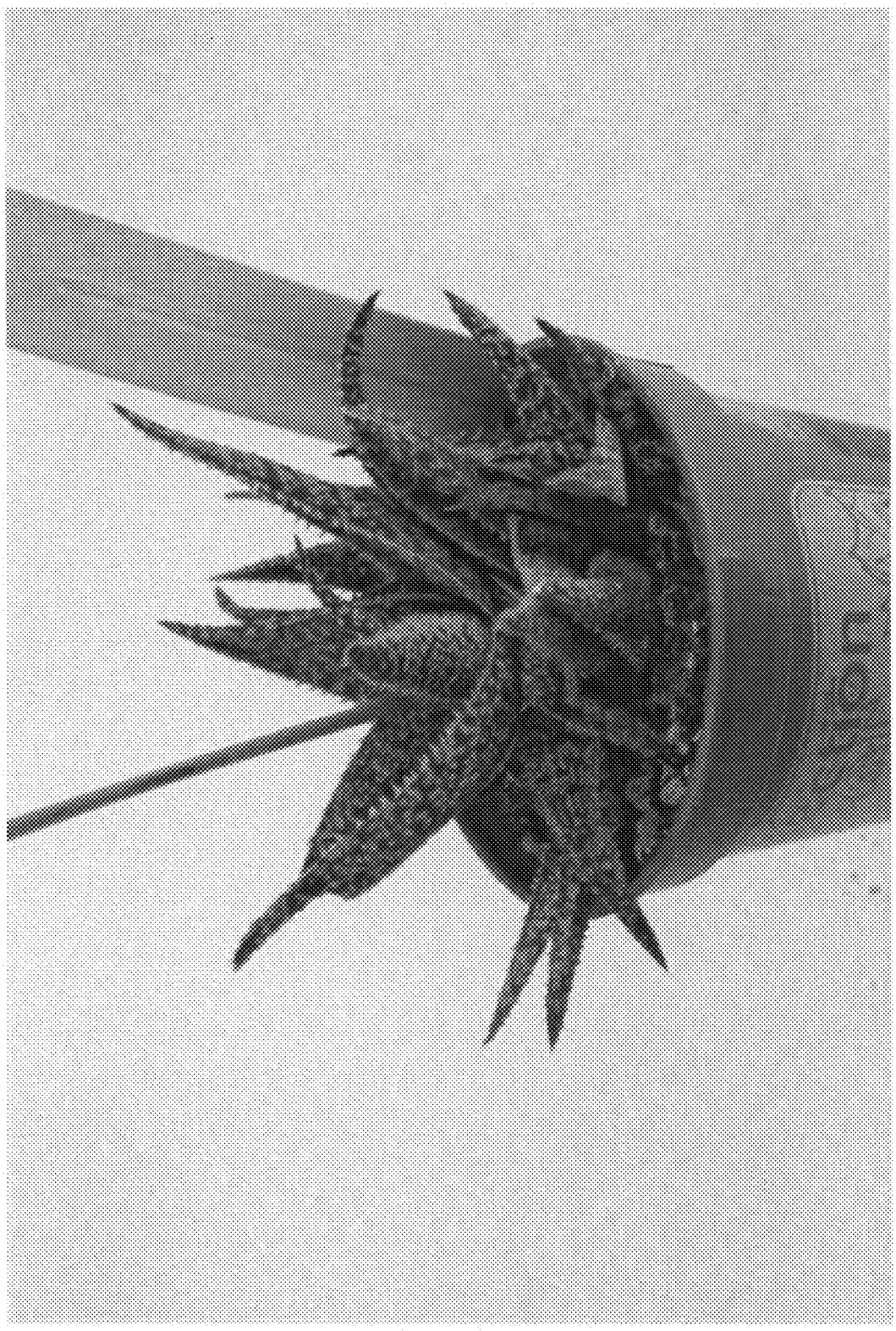

* * * * *